(12) United States Patent
Rhee et al.

(10) Patent No.: US 11,357,510 B2
(45) Date of Patent: Jun. 14, 2022

(54) OCCLUSIVE DEVICES

(71) Applicant: Covidien LP, Mansfield, MA (US)

(72) Inventors: Richard Rhee, Anaheim Hills, CA (US); Earl Bardsley, San Clemente, CA (US)

(73) Assignee: COVIDIEN LP, Mansfield, MA (US)

( * ) Notice: Subject to any disclaimer, the term of this patent is extended or adjusted under 35 U.S.C. 154(b) by 337 days.

(21) Appl. No.: 16/601,101

(22) Filed: Oct. 14, 2019

(65) Prior Publication Data

US 2020/0038032 A1 Feb. 6, 2020

Related U.S. Application Data

(63) Continuation of application No. 14/862,522, filed on Sep. 23, 2015, now Pat. No. 10,478,194.

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12172* (2013.01); *A61B 2017/00526* (2013.01)

(58) Field of Classification Search
CPC ........ A61B 17/12031; A61B 17/12109; A61B 17/12113; A61B 17/12118; A61B 17/12168; A61B 17/12172; A61B 17/12177; A61B 17/12186; A61B 2017/00831; A61B 2017/00526; A61F 2002/823; A61F 2002/825; A61F 2/82; A61F 2/86; A61F 2/88; A61F 2/07; A61F 2/077; A61F 2/072; B21F 45/008; B21F 27/10

See application file for complete search history.

(56) References Cited

U.S. PATENT DOCUMENTS

| | | | |
|---|---|---|---|
| 3,108,593 | A | 10/1963 | Glassman |
| 4,425,908 | A | 1/1984 | Simon |
| 4,619,246 | A | 10/1986 | Molgaard-nielsen et al. |
| 4,655,771 | A | 4/1987 | Wallsten |
| 4,768,507 | A | 9/1988 | Fischell et al. |
| 4,921,484 | A | 5/1990 | Hillstead |
| 4,998,539 | A | 3/1991 | Delsanti |
| 5,026,377 | A | 6/1991 | Burton et al. |

(Continued)

FOREIGN PATENT DOCUMENTS

| | | |
|---|---|---|
| CA | 2607529 A1 | 4/2008 |
| CN | 101472537 A | 7/2009 |

(Continued)

OTHER PUBLICATIONS

European Search Report dated Jan. 29, 2021; European Patent Application No. 20205097.7; 8 pages.

(Continued)

*Primary Examiner* — Jocelin C Tanner
(74) *Attorney, Agent, or Firm* — Fortem IP, LLP; Katrina Marcelo; Mary Fox

(57) ABSTRACT

An implant can include a frame and a mesh component coupled to the frame. The mesh component can define a first porosity, and the frame can define a frame porosity. The combined porosity of the mesh component and the frame can restrict blood flow into the implant.

19 Claims, 6 Drawing Sheets

(56) References Cited

U.S. PATENT DOCUMENTS

| | | | |
|---|---|---|---|
| 5,061,275 A | 10/1991 | Wallsten et al. | |
| 5,064,435 A | 11/1991 | Porter | |
| 5,104,404 A | 4/1992 | Wolff | |
| 5,122,136 A | 6/1992 | Guglielmi et al. | |
| 5,158,548 A | 10/1992 | Lau et al. | |
| 5,222,971 A | 6/1993 | Willard et al. | |
| 5,250,071 A | 10/1993 | Palermo | |
| 5,308,356 A | 5/1994 | Blackshear, Jr. et al. | |
| 5,334,210 A | 8/1994 | Gianturco | |
| 5,354,295 A | 10/1994 | Guglielmi et al. | |
| 5,378,239 A | 1/1995 | Termin et al. | |
| 5,405,379 A | 4/1995 | Lane | |
| 5,425,984 A | 6/1995 | Kennedy et al. | |
| 5,484,444 A | 1/1996 | Braunschweiler et al. | |
| 5,499,981 A | 3/1996 | Kordis | |
| 5,527,338 A | 6/1996 | Purdy | |
| 5,545,208 A | 8/1996 | Wolff et al. | |
| 5,545,209 A | 8/1996 | Roberts et al. | |
| 5,549,635 A | 8/1996 | Solar | |
| 5,624,461 A | 4/1997 | Mariant | |
| 5,634,942 A | 6/1997 | Chevillon et al. | |
| 5,645,558 A | 7/1997 | Horton | |
| 5,662,703 A | 9/1997 | Yurek et al. | |
| 5,669,931 A | 9/1997 | Kupiecki et al. | |
| 5,690,671 A | 11/1997 | Mcgurk et al. | |
| 5,702,419 A | 12/1997 | Berry et al. | |
| 5,713,907 A | 2/1998 | Wholey et al. | |
| 5,725,552 A | 3/1998 | Kotula et al. | |
| 5,728,906 A | 3/1998 | Eguchi et al. | |
| 5,733,294 A | 3/1998 | Forber et al. | |
| 5,741,333 A | 4/1998 | Frid | |
| 5,749,891 A | 5/1998 | Ken et al. | |
| 5,749,919 A | 5/1998 | Blanc | |
| 5,749,920 A | 5/1998 | Quiachon et al. | |
| 5,766,151 A | 6/1998 | Valley et al. | |
| 5,769,884 A | 6/1998 | Solovay | |
| 5,814,062 A | 9/1998 | Sepetka et al. | |
| 5,830,230 A | 11/1998 | Berryman et al. | |
| 5,846,261 A | 12/1998 | Kotula et al. | |
| 5,853,422 A | 12/1998 | Huebsch et al. | |
| 5,855,578 A | 1/1999 | Guglielmi et al. | |
| 5,879,366 A | 3/1999 | Shaw et al. | |
| 5,911,731 A | 6/1999 | Pham et al. | |
| 5,916,235 A | 6/1999 | Guglielmi | |
| 5,925,060 A | 7/1999 | Forber | |
| 5,928,228 A | 7/1999 | Kordis et al. | |
| 5,928,260 A | 7/1999 | Chin et al. | |
| 5,935,148 A | 8/1999 | Villar et al. | |
| 5,935,362 A | 8/1999 | Petrick | |
| 5,941,249 A | 8/1999 | Maynard | |
| 5,944,738 A | 8/1999 | Amplatz et al. | |
| 5,951,599 A | 9/1999 | Mccrory | |
| 5,957,948 A | 9/1999 | Mariant | |
| 5,976,162 A | 11/1999 | Doan et al. | |
| 5,980,554 A | 11/1999 | Lenker et al. | |
| 6,001,092 A | 12/1999 | Mirigian et al. | |
| 6,010,517 A | 1/2000 | Baccaro | |
| 6,024,756 A | 2/2000 | Huebsch et al. | |
| 6,033,423 A | 3/2000 | Ken et al. | |
| 6,036,720 A | 3/2000 | Abrams et al. | |
| 6,059,813 A | 5/2000 | Vrba et al. | |
| 6,063,070 A | 5/2000 | Eder | |
| 6,063,104 A | 5/2000 | Villar et al. | |
| 6,086,577 A | 7/2000 | Ken et al. | |
| 6,093,199 A | 7/2000 | Brown et al. | |
| 6,096,034 A | 8/2000 | Kupiecki et al. | |
| 6,096,073 A | 8/2000 | Webster et al. | |
| 6,099,526 A | 8/2000 | Whayne et al. | |
| 6,106,530 A | 8/2000 | Harada | |
| 6,110,191 A | 8/2000 | Dehdashtian et al. | |
| 6,123,715 A | 9/2000 | Amplatz | |
| 6,139,564 A | 10/2000 | Teoh | |
| 6,152,144 A | 11/2000 | Lesh et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,168,622 B1 | 1/2001 | Mazzocchi | |
| 6,183,495 B1 | 2/2001 | Lenker et al. | |
| 6,190,402 B1 | 2/2001 | Horton et al. | |
| 6,193,708 B1 | 2/2001 | Ken et al. | |
| 6,217,609 B1 | 4/2001 | Haverkost | |
| 6,221,086 B1 | 4/2001 | Forber | |
| 6,261,305 B1 | 7/2001 | Marotta et al. | |
| 6,280,412 B1 | 8/2001 | Pederson, Jr. et al. | |
| 6,306,141 B1 | 10/2001 | Jervis | |
| 6,309,367 B1 | 10/2001 | Boock | |
| 6,322,576 B1 | 11/2001 | Wallace et al. | |
| 6,325,815 B1 * | 12/2001 | Kusleika | A61F 2/0108 606/200 |
| 6,325,820 B1 | 12/2001 | Khosravi et al. | |
| 6,331,184 B1 | 12/2001 | Abrams | |
| 6,332,576 B1 | 12/2001 | Colley et al. | |
| 6,342,068 B1 | 1/2002 | Thompson | |
| 6,344,041 B1 | 2/2002 | Kupiecki et al. | |
| 6,344,048 B1 | 2/2002 | Chin et al. | |
| 6,346,117 B1 | 2/2002 | Greenhalgh | |
| 6,350,270 B1 | 2/2002 | Roue | |
| 6,361,545 B1 | 3/2002 | Macoviak et al. | |
| 6,361,558 B1 | 3/2002 | Hieshima et al. | |
| 6,368,339 B1 | 4/2002 | Amplatz | |
| 6,375,668 B1 | 4/2002 | Gifford et al. | |
| 6,379,372 B1 | 4/2002 | Dehdashtian et al. | |
| 6,383,174 B1 | 5/2002 | Eder | |
| 6,391,037 B1 | 5/2002 | Greenhalgh | |
| 6,409,750 B1 | 6/2002 | Hyodoh et al. | |
| 6,428,558 B1 | 8/2002 | Jones et al. | |
| 6,443,972 B1 | 9/2002 | Bosma et al. | |
| 6,447,531 B1 | 9/2002 | Amplatz | |
| 6,454,780 B1 | 9/2002 | Wallace | |
| 6,506,204 B2 | 1/2003 | Mazzocchi | |
| 6,511,468 B1 | 1/2003 | Cragg et al. | |
| 6,530,934 B1 | 3/2003 | Jacobsen et al. | |
| 6,544,278 B1 | 4/2003 | Vrba et al. | |
| 6,547,804 B2 | 4/2003 | Porter et al. | |
| 6,551,303 B1 | 4/2003 | Van Tassel et al. | |
| 6,569,179 B2 | 5/2003 | Teoh et al. | |
| 6,579,302 B2 | 6/2003 | Duerig et al. | |
| 6,579,303 B2 | 6/2003 | Amplatz | |
| 6,585,748 B1 | 7/2003 | Jeffree | |
| 6,585,756 B1 | 7/2003 | Strecker | |
| 6,589,256 B2 | 7/2003 | Forber | |
| 6,589,265 B1 | 7/2003 | Palmer et al. | |
| 6,592,605 B2 | 7/2003 | Lenker et al. | |
| 6,599,308 B2 | 7/2003 | Amplatz | |
| 6,602,261 B2 | 8/2003 | Greene, Jr. et al. | |
| 6,605,101 B1 | 8/2003 | Schaefer et al. | |
| 6,605,102 B1 | 8/2003 | Mazzocchi et al. | |
| 6,605,111 B2 | 8/2003 | Bose et al. | |
| 6,607,551 B1 | 8/2003 | Sullivan et al. | |
| 6,613,074 B1 | 9/2003 | Mitelberg et al. | |
| 6,626,939 B1 | 9/2003 | Burnside et al. | |
| 6,632,241 B1 | 10/2003 | Hancock et al. | |
| 6,635,068 B1 | 10/2003 | Dubrul et al. | |
| 6,635,069 B1 | 10/2003 | Teoh et al. | |
| 6,652,555 B1 | 11/2003 | Vantassel et al. | |
| 6,652,556 B1 | 11/2003 | Vantassel et al. | |
| 6,666,882 B1 | 12/2003 | Bose et al. | |
| 6,666,883 B1 | 12/2003 | Seguin et al. | |
| 6,669,717 B2 | 12/2003 | Marotta et al. | |
| 6,669,721 B1 | 12/2003 | Bose et al. | |
| 6,676,696 B1 | 1/2004 | Marotta et al. | |
| 6,682,505 B2 | 1/2004 | Bates et al. | |
| 6,682,546 B2 | 1/2004 | Amplatz | |
| 6,689,150 B1 | 2/2004 | Vantassel et al. | |
| 6,689,486 B2 | 2/2004 | Ho et al. | |
| 6,695,876 B1 | 2/2004 | Marotta et al. | |
| 6,698,877 B2 | 3/2004 | Urlaub et al. | |
| 6,699,274 B2 | 3/2004 | Stinson | |
| 6,709,465 B2 | 3/2004 | Mitchell et al. | |
| 6,712,835 B2 | 3/2004 | Mazzocchi et al. | |
| 6,723,112 B2 | 4/2004 | Ho et al. | |
| 6,723,116 B2 | 4/2004 | Taheri | |
| 6,730,108 B2 | 5/2004 | Van Tassel et al. | |
| 6,746,468 B1 | 6/2004 | Sepetka et al. | |

(56) References Cited

U.S. PATENT DOCUMENTS

| | | |
|---|---|---|
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-gawwad |
| RE38,711 E | 3/2005 | Igaki et al. |
| 6,860,893 B2 | 3/2005 | Wallace et al. |
| 6,878,384 B2 | 4/2005 | Cruise et al. |
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | Van Der Burg et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | Van Der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,601,160 B2 | 10/2009 | Richter |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,763,011 B2 * | 7/2010 | Ortiz ............... A61F 2/90 604/509 |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| RE42,625 E | 8/2011 | Guglielmi |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,043,326 B2 | 10/2011 | Hancock et al. |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | Van Tassel et al. |
| 8,261,648 B1 | 9/2012 | Marchand et al. |
| 8,298,257 B2 | 10/2012 | Sepetka et al. |
| 8,333,783 B2 | 12/2012 | Braun et al. |
| 8,425,541 B2 | 4/2013 | Masters et al. |
| 8,430,012 B1 | 4/2013 | Marchand et al. |
| 8,454,681 B2 | 6/2013 | Holman et al. |
| 8,470,013 B2 | 6/2013 | Duggal et al. |
| 8,715,317 B1 | 5/2014 | Janardhan et al. |
| 8,906,057 B2 | 12/2014 | Connor et al. |
| 9,179,918 B2 | 11/2015 | Levy et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,004,511 B2 | 6/2018 | Molaei et al. |
| 10,028,745 B2 | 7/2018 | Morsi |
| 10,478,194 B2 | 11/2019 | Rhee et al. |
| 2001/0000797 A1 | 5/2001 | Mazzocchi |
| 2001/0001835 A1 | 5/2001 | Greene et al. |
| 2001/0007082 A1 | 7/2001 | Dusbabek et al. |
| 2001/0012949 A1 | 8/2001 | Forber |
| 2001/0031981 A1 | 10/2001 | Evans et al. |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0057156 A1 | 3/2003 | Peterson et al. |
| 2003/0074049 A1 | 4/2003 | Hoganson et al. |
| 2003/0114917 A1 | 6/2003 | Holloway et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0044396 A1 | 3/2004 | Clerc et al. |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | Vantassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |

(56) References Cited

U.S. PATENT DOCUMENTS

| | | |
|---|---|---|
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0243882 A1 | 12/2004 | Zhou et al. |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043750 A1 | 2/2005 | Scott et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-gawwad |
| 2005/0222605 A1 | 10/2005 | Greenhalgh et al. |
| 2005/0228434 A1 | 10/2005 | Amplatz et al. |
| 2005/0267511 A1 | 12/2005 | Marks et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0200234 A1 | 9/2006 | Hines |
| 2006/0206199 A1 | 9/2006 | Churchwell et al. |
| 2006/0206200 A1 | 9/2006 | Garcia et al. |
| 2006/0217799 A1 | 9/2006 | Mailänder et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0016283 A1* | 1/2007 | Greenhalgh ............... A61F 2/07 623/1.15 |
| 2007/0021816 A1 | 1/2007 | Rudin |
| 2007/0050017 A1 | 3/2007 | Sims et al. |
| 2007/0066993 A1 | 3/2007 | Kreidler |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0100426 A1 | 5/2007 | Rudakov et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0175536 A1 | 8/2007 | Monetti et al. |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233175 A1* | 10/2007 | Zaver ............... A61F 2/0105 606/200 |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0200946 A1* | 8/2008 | Braun ............... A61M 25/0054 606/198 |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1* | 11/2009 | Rosqueta ......... A61B 17/12113 623/1.15 |
| 2009/0287297 A1 | 11/2009 | Cox |
| 2009/0292348 A1 | 11/2009 | Berez et al. |
| 2009/0318941 A1 | 12/2009 | Sepetka et al. |
| 2009/0318948 A1 | 12/2009 | Davis et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030220 A1 | 2/2010 | Truckai et al. |
| 2010/0036390 A1 | 2/2010 | Gumm |
| 2010/0036481 A1* | 2/2010 | Dubrul ............... A61M 29/02 623/1.42 |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |

(56) References Cited

U.S. PATENT DOCUMENTS

| | | |
|---|---|---|
| 2010/0106178 A1 | 4/2010 | Obermiller et al. |
| 2010/0131002 A1 | 5/2010 | Connor et al. |
| 2010/0144895 A1 | 6/2010 | Porter |
| 2010/0152767 A1 | 6/2010 | Greenhalgh et al. |
| 2010/0185271 A1 | 7/2010 | Zhang |
| 2010/0222802 A1 | 9/2010 | Gillespie, Jr. et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | Mcguckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0130826 A1 | 6/2011 | Cragg et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0204351 A1 | 8/2013 | Cox et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2014/0012307 A1 | 1/2014 | Franano et al. |
| 2014/0058420 A1 | 2/2014 | Hannes et al. |
| 2014/0074151 A1 | 3/2014 | Tischler et al. |
| 2014/0128905 A1 | 5/2014 | Molaei |
| 2014/0135810 A1* | 5/2014 | Divino ............ A61B 17/12118 606/194 |
| 2014/0135817 A1 | 5/2014 | Tischler et al. |
| 2014/0172001 A1 | 6/2014 | Becking et al. |
| 2014/0200648 A1 | 7/2014 | Newell et al. |
| 2014/0243882 A1 | 8/2014 | Ma |
| 2014/0277361 A1 | 9/2014 | Farhat et al. |
| 2014/0277400 A1 | 9/2014 | Wainwright et al. |
| 2014/0316012 A1 | 10/2014 | Freyman et al. |
| 2014/0358178 A1* | 12/2014 | Hewitt ............ A61B 17/12113 606/200 |
| 2014/0371734 A1 | 12/2014 | Truckai |
| 2015/0133989 A1* | 5/2015 | Lubock ............ A61B 17/0057 606/200 |
| 2015/0157331 A1 | 6/2015 | Levy et al. |
| 2015/0173770 A1 | 6/2015 | Warner et al. |
| 2015/0209050 A1 | 7/2015 | Aboytes et al. |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0113786 A1 | 4/2016 | Levy et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |

FOREIGN PATENT DOCUMENTS

| | | |
|---|---|---|
| DE | 1283434 B | 11/1968 |
| DE | 102008028308 A1 | 4/2009 |
| DE | 102010050569 A1 | 5/2012 |
| DE | 102011011510 A1 | 8/2012 |
| EP | 0743047 A2 | 11/1996 |
| EP | 0855170 A2 | 7/1998 |
| EP | 0775470 A2 | 3/1999 |
| EP | 1621148 A1 | 2/2006 |
| EP | 1637176 A1 | 3/2006 |
| EP | 1752112 A1 | 2/2007 |
| EP | 1942972 A1 | 7/2008 |
| EP | 1872742 B1 | 5/2009 |
| EP | 2279023 A2 | 2/2011 |
| EP | 2363075 A1 | 9/2011 |
| EP | 2496299 A2 | 9/2012 |
| EP | 2675402 A2 | 12/2013 |
| EP | 2777640 A1 | 9/2014 |
| EP | 2809262 A1 | 12/2014 |
| FR | 2556210 B1 | 4/1988 |
| FR | 2890306 A1 | 3/2007 |
| JP | 11506686 | 6/1999 |
| JP | 2003520103 A | 7/2003 |
| JP | 2003524434 A | 8/2003 |
| JP | 2004049585 A | 2/2004 |
| JP | 2005522266 A | 7/2005 |
| JP | 2006506201 A | 2/2006 |
| JP | 2008513140 A | 5/2008 |
| JP | 2008541832 A | 11/2008 |
| JP | 4673987 B2 | 1/2011 |
| JP | 2011518023 A | 6/2011 |
| JP | 2014533743 A | 12/2014 |
| JP | 2015091416 A | 5/2015 |
| KR | 20150084959 A | 7/2015 |
| WO | WO 8800813 A1 | 2/1988 |
| WO | WO 9601591 A1 | 1/1996 |
| WO | WO 9726939 A1 | 7/1997 |
| WO | WO 9903404 A1 | 1/1999 |
| WO | WO 9905977 A1 | 2/1999 |
| WO | WO 9908607 A1 | 2/1999 |
| WO | WO 9908743 A1 | 2/1999 |
| WO | WO 9940873 A1 | 8/1999 |

(56) References Cited

FOREIGN PATENT DOCUMENTS

| | | |
|---|---|---|
| WO | WO 9962432 A1 | 12/1999 |
| WO | WO 2000057815 A1 | 10/2000 |
| WO | WO 0174255 A1 | 10/2001 |
| WO | WO 2001093782 | 12/2001 |
| WO | WO 2002000139 | 1/2002 |
| WO | WO 2002071977 | 9/2002 |
| WO | WO 2003037191 | 5/2003 |
| WO | WO 2004085590 A1 | 10/2004 |
| WO | WO 2005117718 A1 | 12/2005 |
| WO | WO 2006026744 A1 | 3/2006 |
| WO | WO 2006034140 A2 | 3/2006 |
| WO | WO 2006034166 A2 | 3/2006 |
| WO | WO 2006052322 A2 | 5/2006 |
| WO | WO 2006091891 A2 | 8/2006 |
| WO | WO 2006119422 A2 | 11/2006 |
| WO | WO 2007047851 A2 | 4/2007 |
| WO | WO 2007076480 A2 | 7/2007 |
| WO | WO 2007095031 A2 | 8/2007 |
| WO | WO 2007121405 A2 | 10/2007 |
| WO | WO 2008022327 A2 | 2/2008 |
| WO | WO 2008109228 A2 | 9/2008 |
| WO | WO 2008151204 A1 | 12/2008 |
| WO | WO 2008157507 A2 | 12/2008 |
| WO | WO 2009008868 A1 | 1/2009 |
| WO | WO 2009076515 A1 | 6/2009 |
| WO | WO 2009132045 A2 | 10/2009 |
| WO | WO 2009134337 A1 | 11/2009 |
| WO | WO 2009135166 A2 | 11/2009 |
| WO | WO 2010028314 A1 | 3/2010 |
| WO | WO 2010030991 A1 | 3/2010 |
| WO | WO 2010147808 A1 | 12/2010 |
| WO | WO 2011057002 A2 | 5/2011 |
| WO | WO 2011057277 A2 | 5/2011 |
| WO | WO 2011066962 A1 | 6/2011 |
| WO | WO 2011130081 A1 | 10/2011 |
| WO | WO 2011153304 A1 | 12/2011 |
| WO | WO 2012068175 A2 | 5/2012 |
| WO | WO 2012112749 A2 | 8/2012 |
| WO | WO 2012166804 A1 | 12/2012 |
| WO | 2013116860 A1 | 8/2013 |
| WO | WO 2014085590 A1 | 6/2014 |
| WO | WO 2017074411 A1 | 5/2017 |
| WO | WO 2018051187 A1 | 3/2018 |

OTHER PUBLICATIONS

European Search Report dated Mar. 9, 2017; European Patent Application No. 16189394,6; 8 pages.

Hill, et al., "Initial Results of the AMPLATZER Vascular Plug in the Treatment of Congenital Heart Disease, Business Briefing." US Cardiology 2004.

Ronnen, "AMPLATZER Vascular Plug Case Study, Closure of Arteriovenous Fistula Between Dee Femoral Artery and Superficial Femoral Vein," AGA Medical Corporation, May 2007.

Thorell, et al.,"Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

* cited by examiner

OCCLUSIVE DEVICES

CROSS-REFERENCE TO RELATED APPLICATION(S)

This application is a continuation of U.S. patent application Ser. No. 14/862,522, filed Sep. 23, 2015, the contents of which are hereby incorporated by reference herein.

BACKGROUND

Field of the Inventions

The present disclosure generally relates to intrasaccular medical devices, and more particularly, to a medical implant having a frame and a mesh component for occluding a target area of a patient's vasculature.

Description of the Related Art

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury or a congenital abnormality. Aneurysms could be found in different parts of the body with the most common being abdominal aortic aneurysms (AAA) and brain or cerebral aneurysms. When the weakened wall of an aneurysm ruptures, it can result in death.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils) or braided ball devices; (iii) using embolic materials to "fill" or "pack" an aneurysm; (iv) using detachable balloons or coils to occlude the parent vessel that supplies the aneurysm; and (v) using stents to divert blood flow away from the aneurysm.

SUMMARY

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Systems and procedures for treating aneurysms can include an implantable device that can be inserted into an aneurysm to facilitate a thrombotic, healing effect. The implantable device can have specific characteristics, including porosity, composition, material, shape, size, interconnectedness, inter-engagement, coating, etc. These characteristics can be selected in order to achieve a desired treatment or placement of the implantable device.

Implants or implantable devices for occluding a target area of a patient's vasculature, such as an aneurysm, can comprise a frame or frame component and one or more mesh components for mesh components that are coupled to the frame. The implantable device can be configured to provide an atraumatic, high surface area region that can promote endothelialization when the implantable device is implanted into a body lumen. The high surface area coverage can be created using a mesh component positioned along a given region of the frame. In some embodiments, a single mesh component can be coupled to the frame that has a generally constant porosity. However, the single mesh component can have a variable porosity. Further, multiple mesh components can be coupled to the frame that each have different porosities.

In some embodiments, the implantable device can have an average porosity that changes from a first end or region of the device to a second end or region of the device. Different regions of the device can define different porosities due to the presence of one or more mesh components in a given region or based on the porosity of the frame itself in a given region. Some embodiments therefore provide an implantable device that can have a first porosity in a distal region and a second porosity and a proximal region based on the presence of the mesh component in the proximal region of the device.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Clause 1. An implant for occluding a target area of a patient's vasculature, comprising: a frame comprising a plurality of braided filaments that define a plurality of openings, the plurality of filaments and openings collectively defining a frame porosity, the frame comprising a distal region and a proximal region, the frame being expandable from a compressed configuration to an expanded configuration; and a mesh component coupled to the frame along at least the proximal region thereof, the mesh component comprising a plurality of filaments and a plurality of openings, the plurality of filaments and openings collectively defining a first porosity permitting blood flow therethrough, the first porosity being less than the frame porosity, such that blood flow into the implant is more restricted along the proximal region than along the distal region of the frame.

Clause 2. The implant of Clause 1, wherein the mesh component is a first mesh component, and the implant further comprises a second mesh component coupled to the frame along the proximal region.

Clause 3. The implant of Clause 2, wherein the second mesh component comprises a second porosity, different from the first porosity.

Clause 4. The implant of any of Clauses 2-3, wherein first and second mesh components overlie respective first and second openings in the frame, the first opening being adjacent to the second opening.

Clause 5. The implant of any of Clauses 2-4, wherein the second mesh component is positioned adjacent to the first mesh component.

Clause 6. The implant of any of Clauses 2-5, wherein an edge of the second mesh component borders an edge of the first mesh component.

Clause 7. The implant of any of Clauses 2-6, further comprising a third mesh component coupled to the frame along the proximal region.

Clause 8. The implant of Clause 7, wherein the third mesh component is positioned adjacent to the first mesh component.

Clause 9. The implant of any of Clauses 7-8, wherein the third mesh component comprises a third porosity, different from the first porosity.

Clause 10. The implant of any of Clauses 7-9, wherein the second mesh component comprises a second porosity, and the third mesh component comprises a third porosity, different from the second porosity.

Clause 11. The implant of Clause 10, wherein the first porosity is different from the second and third porosities.

Clause 12. The implant of any of Clauses 1-11, wherein the mesh component comprises a strip of material.

Clause 13. The implant of any of Clauses 1-12, wherein the frame comprises a globular shape.

Clause 14. The implant of Clause 13, wherein the frame comprises a spherical shape.

Clause 15. The implant of any of Clauses 13-14, wherein the frame comprises a rounded first portion and a substantially cylindrical second portion.

Clause 16. The implant of any of Clauses 1-15, wherein the mesh component is fixedly coupled to the frame at a plurality of coupling points.

Clause 17. The implant of Clause 16, wherein the mesh component is welded to the frame at the plurality of coupling points.

Clause 18. The implant of any of Clauses 1-17, wherein the mesh component comprises a braided material.

Clause 19. The implant of any of Clauses 1-18, wherein the mesh component is positioned along an exterior of the frame.

Clause 20. The implant of any of Clauses 1-19, wherein the frame and the mesh component are laminated together.

Clause 21. An implant for occluding a target area of a patient's vasculature, comprising a braided frame comprising filaments that intersect each other to define openings, the filaments and openings collectively defining a frame porosity, the frame being expandable from a compressed configuration to an expanded configuration, and a mesh component coupled to the frame, the mesh component comprising filaments and openings that collectively define a first porosity permitting blood flow therethrough, the first porosity being less than the frame porosity, for restricting blood flow into the implant.

Clause 22. The implant of Clause 21, wherein the mesh component is a first mesh component, and the implant further comprises a second mesh component coupled to the frame.

Clause 23. The implant of Clause 22, wherein the second mesh component comprises a second porosity, different from the first porosity.

Clause 24. The implant of any of Clauses 22-23, wherein first and second mesh components overlie respective first and second openings in the frame, the first opening being adjacent to the second opening.

Clause 25. The implant of any of Clauses 22-24, wherein the second mesh component is positioned adjacent to the first mesh component.

Clause 26. The implant of any of Clauses 22-25, wherein an edge of the second mesh component borders an edge of the first mesh component.

Clause 27. The implant of any of Clauses 22-26, further comprising a third mesh component coupled to the frame along the proximal region.

Clause 28. The implant of Clause 27, wherein the third mesh component is positioned adjacent to the first mesh component.

Clause 29. The implant of any of Clauses 27-28, wherein the third mesh component comprises a third porosity, different from the first porosity.

Clause 30. The implant of any of Clauses 27-29, wherein the second mesh component comprises a second porosity, and the third mesh component comprises a third porosity, different from the second porosity.

Clause 31. The implant of Clause 30, wherein the first porosity is different from the second and third porosities.

Clause 32. The implant of any of Clauses 21-31, wherein the mesh component surrounds substantially all of the frame.

Clause 33. The implant of any of Clauses 21-32, wherein the mesh component is disposed along an interior of the frame.

Clause 34. The implant of any of Clauses 21-33, wherein the mesh component is disposed along an exterior of the frame.

Clause 35. The implant of any of Clauses 21-34, wherein the mesh component is fixedly coupled to the frame at a plurality of coupling points.

Clause 36. The implant of any of Clauses 21-35, wherein the frame and the mesh component are welded together.

Clause 37. The implant of any of Clauses 21-36, wherein the pluralities of first and second filaments are interwoven to form a single layer.

Clause 38. The implant of any of Clauses 21-37, wherein the implant comprises a globular shape.

Clause 39. The implant of Clause 38, wherein the implant comprises a spherical shape.

Clause 40. The implant of any of Clauses 38-39, wherein the implant comprises a rounded first portion and a substantially cylindrical second portion.

Clause 41. A method of operating an implant assembly, comprising: closing an end a tubular braid to a substantially closed configuration using a tie, the tubular braid comprising filaments that intersect to define openings, the filaments and openings collectively defining a frame porosity; while holding the end substantially closed, inserting a form into an open end to position the braid around the form; setting a device frame shape based on the form provide an implant; and coupling a mesh component onto the implant, the mesh component comprising filaments and openings that collectively define a first porosity permitting blood flow therethrough, the first porosity being less than the frame porosity, for restricting blood flow into the implant.

Clause 42. The method of Clause 41, wherein the coupling comprises laminating the mesh component onto the tubular braid.

Clause 43. The method of any of Clauses 41-42, wherein the coupling comprises welding the mesh component to the tubular braid.

Clause 44. The method of any of Clauses 41-43, wherein the mesh component comprises a first mesh component, and the coupling comprises coupling a second mesh component to the implant adjacent to the first mesh component.

Clause 45. The method of Clause 44, wherein the coupling comprises coupling a third mesh component to the implant.

Clause 46. The method of any of Clauses 41-45, wherein the coupling comprises positioning the mesh component along an exterior of the implant.

Clause 47. The method of any of Clauses 41-46, wherein the closing comprises collapsing a midsection of a tubular braid to a substantially closed configuration using the tie and inverting a first tubular section of the tubular braid over the tie at the midsection to produce dual layers in the braid such that the braid has a tubular configuration with a closed end at the midsection and an open end opposite the midsection.

Clause 48. The method of any of Clauses 41-47, further comprising removing the tie from the braid.

Clause 49. The method of Clause 47, wherein the removing the tie comprises burning away the tie during heatsetting.

Clause 50. The method of any of Clauses 41-49, further comprising removing the form from the braid.

The method of any of Clauses 41-50, wherein the removing comprises removing the form in one piece.

Clause 52. An implant having any of the features of any of the previous Clauses.

Clause 53. A method of manufacturing any of the implants or assemblies of any of the previous Clauses.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Figure 1:
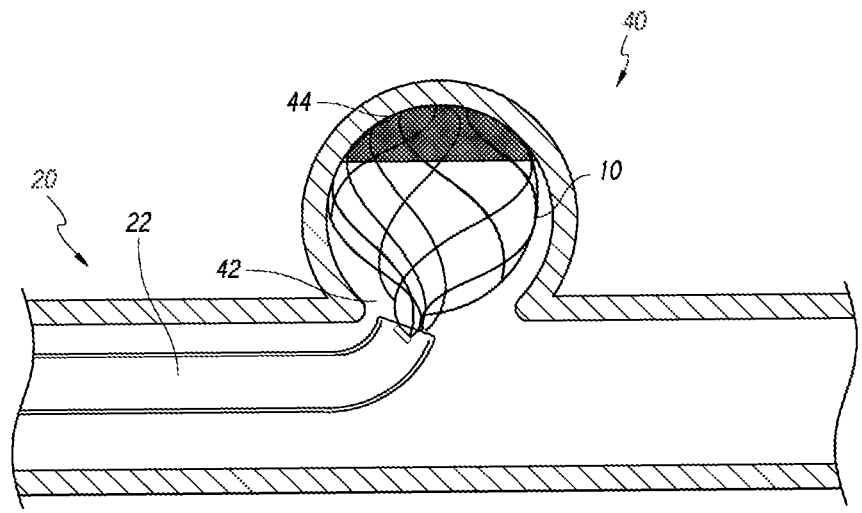
FIG. 1 is a side cross-sectional view illustrating deployment of a device into an aneurysm, according to some embodiments.

Referring now to the figures, FIG. 1 is a side cross-sectional view illustrating deployment of a device into an aneurysm, according to some embodiments. As shown, a device 10 can be advanced to a target aneurysm 40 using a device assembly 20. The device 10 can be advanced from a catheter 22 of the assembly 20 and through a neck 42 of the aneurysm 40 toward a fundus 44 of the aneurysm 40.

Figure 2:
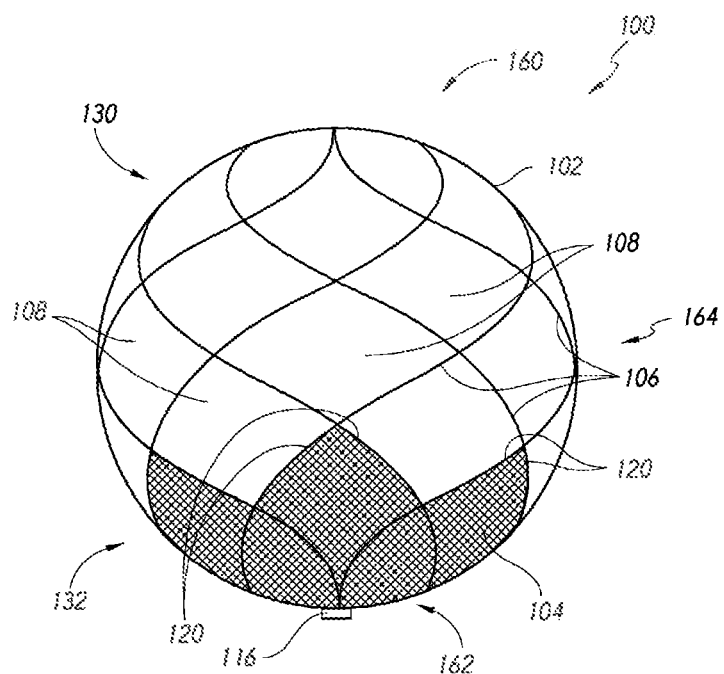
FIG. 2 is a schematic view of an embodiment of an implantable device having a frame and a mesh component, according to some embodiments.

FIG. 2 illustrates an implantable device 100 that comprises a frame 102 and a mesh component 104. The mesh component 104 is coupled to filaments 106 that make up the frame 102. For example, the frame 102 can be formed from a plurality of braided filaments 106 that intersect with each other to provide a plurality of openings 108 along the exterior of the frame 102. The filaments 106 can be coupled together at an end using a suture, hub, or marker band 116, such as through the manufacturing method disclosed in FIGS. 9A-9D. The frame 102 can be formed from as few as six (6) filaments to achieve an easily compressible frame while providing a scaffold to which the mesh component 104 is coupled. The openings 108 can be defined as the voids in the exterior surface of the frame 102 that are bounded by the filaments 106. Similarly, the mesh component 104 can be formed from a plurality of braided filaments that intersect with each other to provide a plurality of openings. The materials used for the frame 102 and/or the mesh component 104 can comprise any known biocompatible or biodegradable materials including stainless steel, nitinol, cobalt chromium, or poly lactic-co-glycolic acid (PLGA).

As illustrated in FIG. 2, the mesh component 104 can be coupled to the frame 102 in order to extend across one or more openings 108 of the frame 102. In so doing, the mesh component 104 can extend over or overlap with one or more filaments 106. The mesh component 104 can be coupled to each and every filament 106 that the mesh component 104 overlaps, according to some embodiments. However, the mesh component 104 may also be coupled to only a portion of the filaments 106 that the mesh component 104 overlaps, and in some cases, to at least one (but not each) of the filaments.

The mesh component 104 shown in FIG. 2 extends across openings of the frame and couples to filaments that form an outer border of the openings over which the mesh component extends. These borders, shown as element 120 in FIG. 2, represent the attachment points between the mesh component 104 and the frame 102. As noted above, the mesh component 104 can be coupled to each of the filaments of the frame 102 that the mesh component 104 overlaps. However, the frame 102 can be coupled to only a few of the filaments of the frame 102 that the mesh component 104 overlaps, according to some embodiments.

Referring still to FIG. 2, the frame 102 can define a distal region 130 and a proximal region 132. The distal and proximal regions 130, 132 can be opposing regions of the device 100. In some embodiments, the mesh component 104 can extend along either or both of the distal and proximal regions 130, 132. The distal and proximal regions 130, 132, as generally shown in FIG. 2, 132 can represent either a minority or majority of the overall surface area of the device 100. The distal and proximal regions 130, 132 can, in some embodiments, be distinguished based on not only the location of the region on the device, but may also be distinguished based on physical aspects of the device, such as shape, frame properties, filament configuration, or other such measures.

The mesh component 104 can be coupled to the implantable device 100 by a variety of mechanical, chemical, and thermal methods well known in medical device manufacture. Depending on the materials selected for implant manufacture, the mesh component 104 can be spot welded, partially melted or heated, or coupled using an adhesive or glue. Alternatively, the mesh component 104 can be coupled to the frame 102 by weaving, threading, or otherwise interconnecting the mesh component 104 with one or more filaments 106 of the frame 102. In some embodiments, the coupling between the mesh component 104 and the filaments 106 can require or utilize additional components or materials. Such embodiments can, for example, utilize sutures or ties to couple the mesh component 104 to filaments 106.

In some embodiments, the mesh component 104 can be laminated to the frame 102 by application of pressure and/or heat, adhesives, or other bonding methods, such as those described above. Further, in some embodiments, a lamination of multiple mesh layers with at least one frame layer can be achieved. As discussed herein, a variety of coatings and other materials can be applied to the structure of the implantable device 100, which can also function to maintain an engagement between the mesh component 104 and the frame 102.

In some embodiments, it is desirable to pretreat the one or more filaments 106 and/or at least a portion of the mesh component 104 to enhance the coupling process. For example, one or more of the filaments 106 (or at least a portion of the frame 102) and/or at least a portion of the mesh component 104 can be pretreated to modify a structural property, such as surface roughness, and/or to add a coating thereto. The surface roughness can be increased by passing a filament and/or a portion of the mesh component through a particulate or chemical bath or otherwise physically contacting a filament and/or the mesh component, e.g., as individual wires prior to being woven into the structure of the frame 102 or prior to being woven into the structure of the mesh component 104. Further, one or more of the filaments 106 (or at least a portion of the frame 102) and/or at least a portion of the mesh component 104 can be coated, e.g., as individual wires, prior to attempting to couple the frame 102 and the mesh component 104. For example, a filament and/or a portion of the mesh component can be coated with a urethane prior to attempting to couple the frame 102 and the mesh component 104. Thus, if one or both of a filament or the mesh component has a coating, heat can be applied during the coupling process to cause the coating (e.g., a urethane) to melt and couple the frame 102 and the mesh component 104 together.

In embodiments the implantable device 100 may vary in porosity gradually, as through a single mesh component comprised of varying pitch, or through the combination of several mesh components 104 coupled to the frame 102. When coupled to the frame 102 along at least the proximal region 132, as illustrated in FIG. 2, the porosity of the implantable device 100 changes from the distal region 132 to the proximal region 132. Therefore, because the porosity of the implantable device 100 is greater along the distal region 130 than along the proximal region 132, blood flow into the implantable device 100 can be more restricted along the proximal region 132 than along the distal region 130. Using this unique configuration, a clinician can position the implantable device 100 within the vasculature, for example positioning the proximal region 132 at the neck of an aneurysm to significantly reduce blood flow into the weakened structure and promote resultant endothelialization in the aneurysm.

Figure 3:
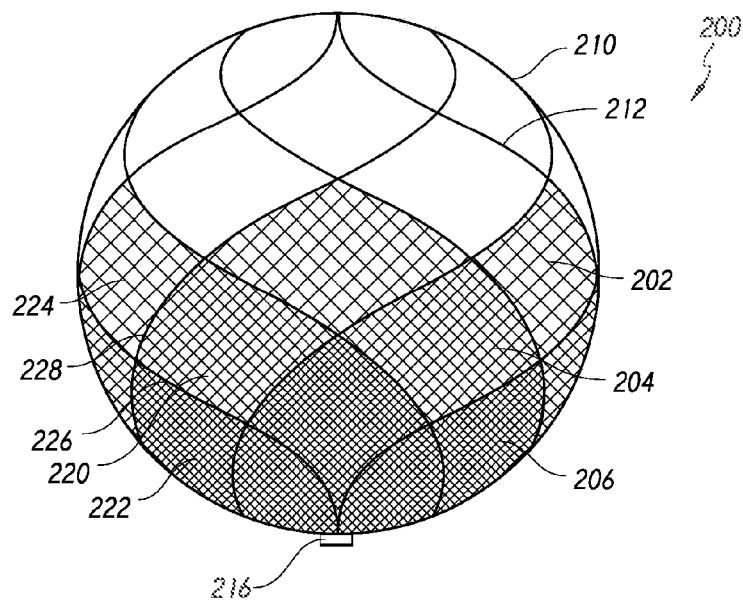
FIG. 3 is a schematic view of an implantable device wherein the mesh component comprises a plurality of individual mesh components having different porosities, according to some embodiments.
Figure 6:
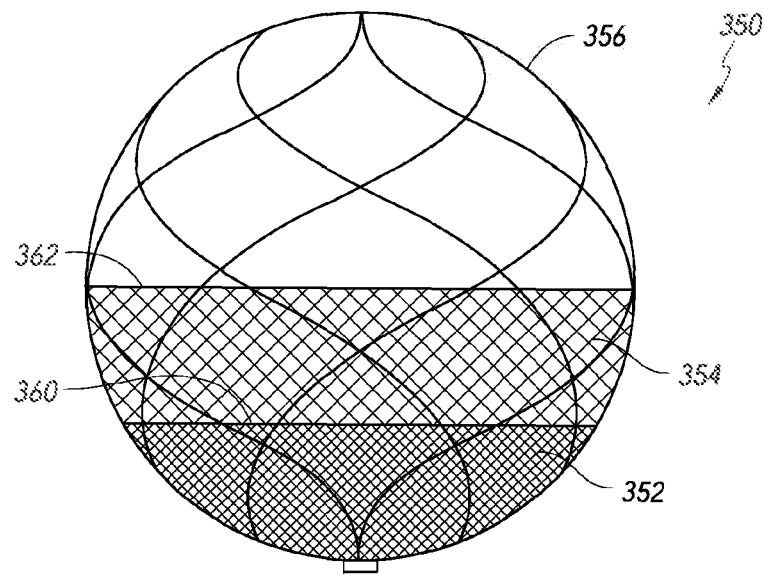

Additionally, an implantable device can comprise more than two regions, such as three, four, five, or more regions, as shown, for example, in FIGS. 3 and 6. Regions of the device can also begin or end based on the presence of a mesh component. Thus, a region of the implantable device can and where one or more mesh components and support begins, thus giving rise to a different region of the device. Accordingly, a device that has a single patch of mesh component can have a distal region defined as the region of the frame along which the mesh component extends and a proximal region, defined as the remaining surface area of the frame.

As it used herein, the term "porosity" can refer to the surface porosity of the implantable device. The surface porosity can be defined as the ratio of empty space (i.e., the surface area of the openings in the mesh component and/or frame) and the total surface area of a given region of the device. In order to calculate the porosity of the implantable device along a specific region of the frame covered by mesh component, the surface area of the openings may be found by first determining the total surface area of filaments in the specific region, accounting for all filaments in the specific region, and calculating a topographical or 2-D representation of total filament area, based on the dimensions (width or diameter and length) of filaments of the frame and/or the dimensions (width or diameter and length) of filaments of the mesh component. The total surface area of the frame and/or mesh component can then be subtracted from the total surface area of the given region in order to provide a resulting surface area of the openings in the given region.

In calculating the porosity of a given region or section of the device, a person of skill in the art can use images of a given device to guide or facilitate the calculation of the openings surface area and total surface area ratio. Such a calculation can rely on known information regarding the size and/or quantity of fibers or filaments in the frame and/or mesh component used in the implantable device.

FIGS. 2-3 illustrate that in some embodiments, implantable devices can be provided in which the mesh component comprises a plurality of panels that extend partially or fully across the frame and/or provide differing porosities in order to create an implantable device that has specific porosity characteristics at one or more locations along the implantable device.

For example, as shown in FIG. 2, the mesh component 104 of the implantable device 100 is coupled to a frame of the device 100. In such an embodiment, the mesh component can define a single or generally constant porosity.

As shown in FIG. 2, in accordance with some embodiments, the frame 102 (as well as any of the frames disclosed herein) can be configured such that a distal region 160 and a proximal region 162 each represent "an end" of a "braid ball" whereat the filaments 106 of the frame 102 converge, thereby creating a relatively lower porosity when compared to a central region 164 of the frame 102. As such, the application or coupling of the mesh component 104 to the proximal region 162 can cause the distal region 162 to have a much lower porosity than the proximal region 160. However, the porosity of the proximal region 162 can change from a relatively higher porosity along the border of the distal region 162 with the central region 164 when compared to the porosity at end 168 of the distal region 162 of the device 100. The change in porosity of the device along the distal region 162, even though the mesh component 104 may define a substantially constant porosity, can be attributed to the convergence of filaments 106 towards each other as they approach the end 168 of distal region 162 of the implant 100.

In light of potential variable porosity structures of frames formed from tubular braided materials, in which opposing ends of the braid are collapsed, thereby causing filaments of the braid to converge towards each other and create regions of decreased porosity, as discussed above with respect to "braid balls," some embodiments can be configured such that one or more mesh components is coupled to the frame and defines a variable porosity that, when summed or combined with the porosity of the underlying or overlying section of the frame, defines a porosity that is substantially constant along one or more sections or substantially the entirety of the surface area of the implantable device. Accordingly, some embodiments can provide implantable devices having a braided material whose variable porosity is offset by a mesh component having a variable porosity such that the composite porosity of the frame and the mesh component at any given location in a section or anywhere along the surface of the implantable component defines a substantially constant porosity.

FIG. 3 illustrates an embodiment of an implantable device 200 in which a plurality of mesh components or panels 202, 204, 206 have been coupled to a frame 210 of the device 200. The frame 210 can be formed from a braided material such that filaments 212 of the frame 210 converge at opposing ends or poles of the frame 210, as discussed above with respect to FIG. 2. The filaments 212 can be coupled together at an end using a suture, hub, or marker band 216, such as through the manufacturing method disclosed in FIGS. 9A-9D. The embodiment illustrated in FIG. 3 illustrates an example in which the device 200 has a variable porosity profile. FIG. 3 illustrates three different porosity panels 202, 204, 206 coupled to frame 210. Although shown in gradient manner of decreasing porosity from the central region to the proximal region, a skilled artisan will appreciate that any combination or number of varying porosity panels can be envisioned to achieve a desired porosity of the entire implantable device 200.

For example, FIG. 3 illustrates that a plurality of mesh components can be coupled to the frame 210 in an adjoining or abutting relationship with respect to each other. Thus, a given mesh component 220 can border with two different mesh components 222, 224. For example, the mesh component 220 can be coupled to a filament 226, 228 that acts as the boundary for the openings across which the respective mesh components 220, 222, 224 extend. Further, not only may different mesh components be positioned adjacent to each other along sections or regions of the frame, but as generally represented in FIG. 3, each of the mesh components 220, 222, 224, can have different porosities.

Figure 4:
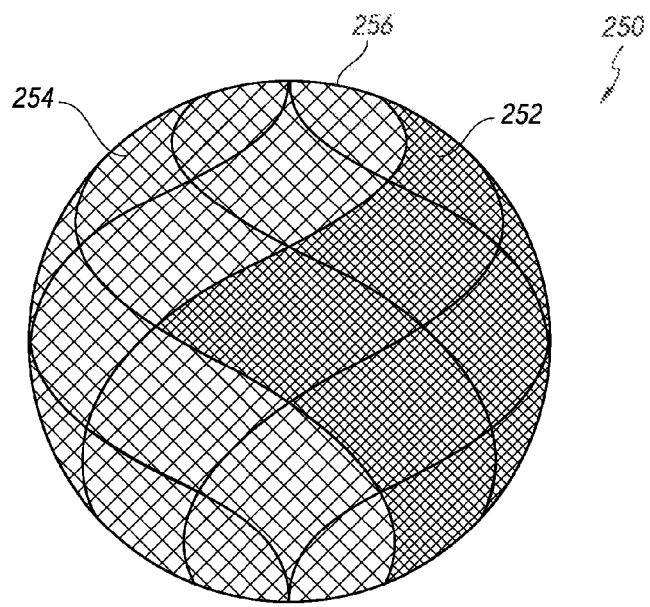
FIG. 4 is a schematic view of yet another implantable device wherein the mesh component comprises a pair of mesh components extending along the entire frame and having different porosities, according to some embodiments.

FIG. 4 illustrates yet another implantable device 250 that comprises a first mesh component 252, a second mesh component 254, and a frame 256 to which the first and second mesh components 252, 254 are coupled. The first and second mesh components 252, 254 can collectively extend across the entire surface area of the generally spherical geometry of the frame.

As shown in FIG. 4, two or more mesh components 252, 254 can be used to establish a given porosity characteristic for the device 250 at specific locations of the device 250. The mesh components used in such embodiments can have substantially constant porosities along at least a portion thereof and/or have variable porosities, as discussed herein.

The one or more mesh components can be coupled to the frame along an outer aspect or surface of the frame, such that the mesh component represents an outermost layer coupled to the frame, or along an inner aspect or interior of the frame, such that the frame generally encloses the mesh component within an inner volume of the frame or is coupled to the mesh component primarily along an interior-facing surface of the frame.

Figure 5:
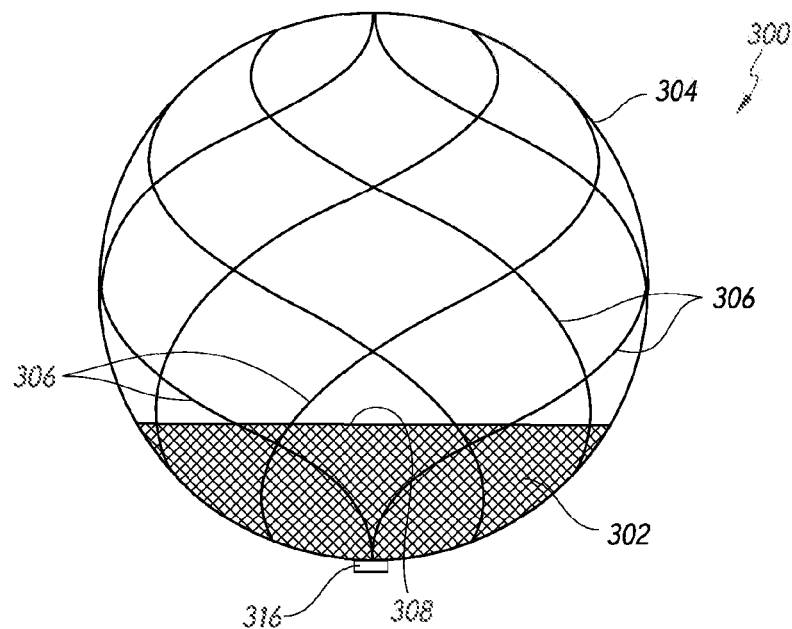
FIGS. 5 and 6 illustrate schematic views of implantable devices having one or more strips of mesh component coupled to the frames thereof, according to some embodiments.

FIGS. 2-4 generally illustrate that the mesh component can be configured to cover substantially the entirety of an opening of the frame such that the mesh component extends across the total surface area of a given opening. Referring now to FIGS. 5 and 6, yet additional embodiments of the implantable device are provided. In some embodiments, the mesh component extends across openings of the frame such that the mesh component covers between about 30% to about 70% of the total surface area of the opening. Accordingly, the mesh component can be coupled to the frame without specifically outlining borders of the mesh component with respective filaments of the frame. The mesh component can therefore, as in the embodiments illustrated above, still be coupled to one or more filaments of the frame, but may have less of an interconnection with the frame along the perimeter or edge of the mesh component than in the embodiments discussed above. Nevertheless, sufficient coupling can be achieved between the mesh component and the filaments so as to enable such embodiments to effectively achieve an integrated or composite unit. Additionally, in order to further ensure interconnectedness between the frame and the mesh component, as with other embodiments, the mesh component can be disposed within and coupled to an inner aspect or surface of the filaments of the frame.

With particular reference to FIG. 5, an implantable device 300 can comprise a mesh component 302 (e.g., a strip of mesh component) that is coupled to a frame 304. The mesh component 302 can comprise an edge 308 that extends generally transversely relative to filaments 306 of the frame 304. The filaments 306 can be coupled together at an end using a suture, hub, or marker band 316, such as through the method disclosed in FIGS. 9A-9D. The mesh component 302 or strip can have a substantially constant porosity or can comprise a variable porosity. The mesh component 302 can be coupled to the filaments 306 along areas in which the mesh component 302 overlaps with the filaments 306. However, less than a majority (e.g., less than 50%, less than 20%, or less than 10%) of the perimeter or edge 308 of the mesh component 302 can be directly coupled to the filaments 306. (Such an arrangement can contrast with the general arrangement illustrated in the embodiments shown in FIGS. 2-4.)

FIG. 6 illustrates another implantable device 350 in which the device 350 comprises first and second mesh components 352, 354 (e.g., strips of mesh component) that are coupled to a frame 356. The first and second mesh components 352, 354 can each overlap filaments of the device 350, and can be spaced apart from each other on the frame 356, or positioned abutting each other. The first and second mesh components 352, 354 can comprise different porosities, substantially constant porosities, or variable porosities.

The first and second mesh components 352, 354 can extend adjacent to each other along the frame 356. However, some embodiments can be provided in which different mesh components extend along the frame in different locations of the frame. Otherwise, FIG. 6 illustrates an embodiment that demonstrates that the perimeter or edge of the mesh components 360, 362 can traverse openings of the frame 356 in a manner similar to that described in FIG. 5, which discussion will not be repeated here for brevity.

Figure 7:
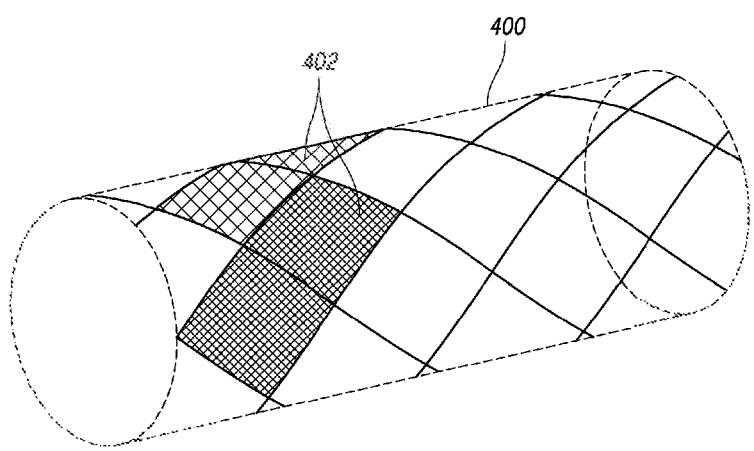
FIGS. 7 and 8 illustrate implantable devices in a pre-assembled state, wherein the implantable devices comprise differing mesh components and/or differing porosities of the mesh components, according to some embodiments.
Figure 8:
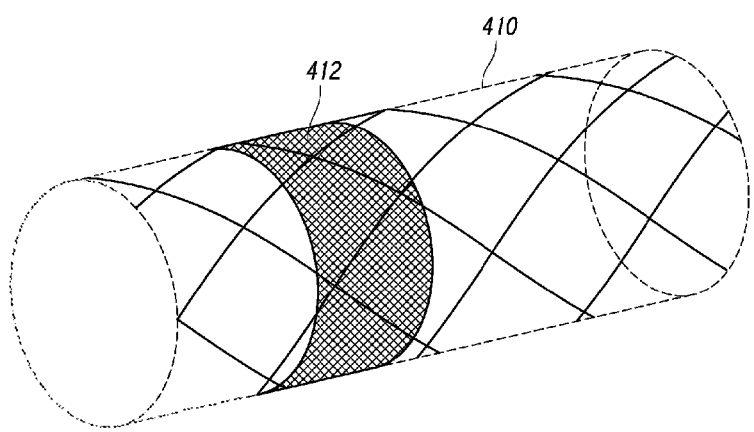

In accordance with some embodiments, methods are provided for forming devices having one or more of the features disclosed herein. The frame and the mesh component can be coupled to each other before or after the frame is formed into a globular component, such as a spherical component. For example, FIGS. 7 and 8 illustrate intermediate configurations of implantable devices in which the devices are formed from a braided tubular or laser cut material. For example, in FIG. 7, a tubular component 400 can serve as the frame for the device and one or more mesh components 402 can be coupled to the tubular component 400, in a manner as illustrated in FIGS. 2-4. Further, FIG. 8 illustrates another tubular component 410 to which a mesh strip 412 is coupled, in a manner similar to that illustrated above with respect to FIGS. 5 and 6.

In accordance with some embodiments, when the frame comprises a braided material (i.e., when the frame is formed using a tubular braid), one of the advantages provided by some embodiments includes the ability to use any of a variety of braid and/or wire configurations. For example, the tubular braid can be formed using as few as 4, 5, or 6 wires. A distinct advantage of some embodiments is a minimal frame with the minimal amount of braid mesh. Another advantage of some embodiments is the substantially reduced profile possible during advancement of the device compared to other devices that use 36, 72, 144, or more wires. Such a reduced profile enables some embodiments to be delivered through much lower-sized catheters, such as 6 Fr, 5 Fr, or 4 Fr. The number of wires can be determined by counting the number of wire ends at the end of the braided tube. In some embodiments having a lower number of wires, e.g., 12 or fewer wires, the primary function of the frame is to provide structural and expansion characteristics. Thus, in such embodiments, the mesh component can primarily provide a desired porosity profile for the implantable device.

In any of the embodiments disclosed herein, the mesh component can optionally comprise a polymer cover, layer, or coating that is applied to the frame after the frame is in a rounded or globular configuration, as shown in FIGS. 2-6, or to the tubular member before the frame is assembled, as discussed and shown with respect to FIGS. 7-9D. For example, after the frame is formed or beforehand (when still in tubular form), the polymer cover can be laser machined to create a pattern of holes in the polymer cover. The pattern of holes can provide a substantially constant or variable porosity in the polymer cover. The polymer cover can comprise any of a variety of polymers, including but not limited to ePTFE, polyurethane, urethane, silicone, and/or others known in the art. Further, in some embodiments, the device can comprise a mesh component and a coating, such as a drug-eluting coating.

In accordance with some embodiments, a method of manufacturing the implantable device can be performed as illustrated in FIGS. 9A-9D. After a suitable tubular component 430 has been formed, including both an underlying frame, mesh or braid pattern 432 and a mesh component 434, the tubular component 430 is positioned over a wire 440 (i.e., the wire 440 is inserted into an inner lumen of the tubular member 430). Thereafter, as illustrated, in FIG. 9A, the tubular member can be closed or tied down onto the wire member 440 using a suture 442, thereby drawing a midsection 446 of the tubular member 430 toward the wire 440.

Figure 9A:
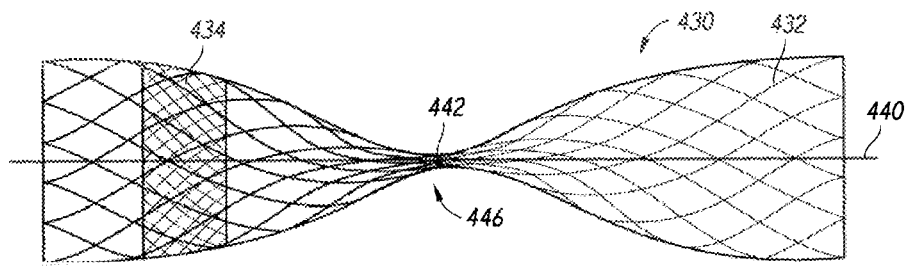
FIGS. 9A-9D illustrate schematic steps m a method of forming an implantable device using a tubular braid material, according to some embodiments.
Figure 9B:
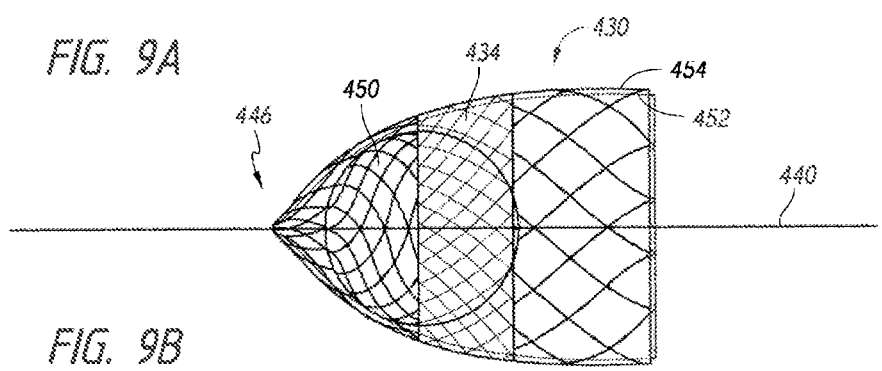

Thereafter, in FIG. 9B, a form 450 can be inserted into the lumen of the tubular member 430 and one end of the tubular member can be everted over the midsection 446 until the everted section of the tubular member forms an outer layer over the other section of the tubular member 430. Accordingly, the tubular member can thereby form inner and outer layers 452, 454. In accordance with some embodiments, the mesh component 434 can be interposed between the inner and outer layers 452, 454.

Other compression forms and methods for positioning the tubular member 430 can be used, such as those described in U.S. patent application Ser. No. 13/048,648, filed on Mar. 15, 2011, the entirety of which is incorporated herein by reference.

Figure 9C:
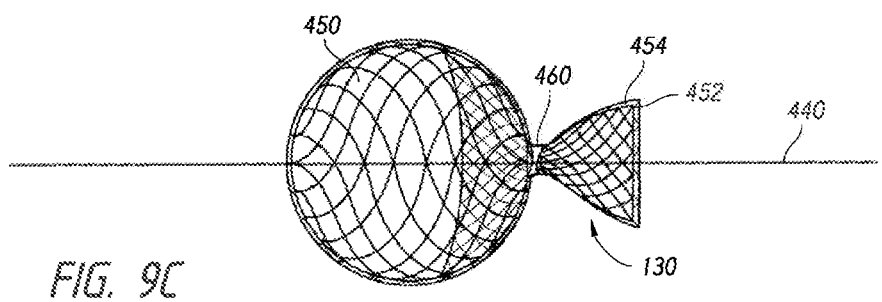
Figure 9D:
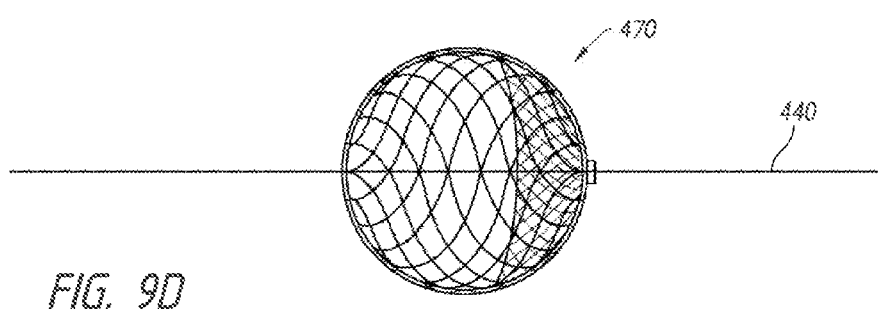

FIG. 9C illustrates that the inner and outer layers 452, 454 can be stretched and drawn around the form 450 and fastened using a suture, hub, or marker band 460 or suitable compression form equipment, as discussed in the above-noted that patent application. Thereafter, the device can be heat set (e.g., nitinol braid can be heat set at 550° C. for five minutes). During the heat setting process, suture material can be burned away, removing any impediment for achieving a zero or near-zero radius bend at the fold at the central region 446. Thereafter, additional material 462 that remains after heat setting the device shape can be trimmed off, as shown in FIG. 9D, thereby leaving a completed implant shape 470. In such a manufacturing method, the finished implant 470 can thereby enclose one or more mesh components or layers with one or more layers of frame components. For example, the mesh component can be coupled to an inner surface or aspect of a tubular component prior to beginning assembly of the device. During assembly of the device with such a tubular component, the tubular component can be everted over the portion of the tubular component to which the mesh component is coupled, thereby enclosing the mesh component between a dual layer of framing components or filaments.

In implementing the methods for manufacturing implantable devices in accordance with some embodiments disclosed herein, the configuration, size, porosity profile, and number of mesh components can be varied or modified in order to achieve a final implantable device having desired porosity characteristics. Some of the porosity characteristics have been illustrated above with respect to FIGS. 2-6, and can be modified as discussed herein.

Delivery Methods

Furthermore, delivery systems and procedures can be implemented for delivering an implantable device comprising one or more implantable devices, as discussed herein. Further, a system and method are provided for delivery of an implantable device to an aneurysm and/or recapturing the device for removal or repositioning.

According to some embodiments, one or more of implantable devices can be released into a target aneurysm and, in some embodiments, specifically oriented relative to the aneurysm ostium or neck and/or one or more perforating vessels (e.g., perforating arteries or arterioles) adjacent to the aneurysm.

In some embodiments, the implantable device can be released into the target vasculature and mechanically expanded using a balloon or other device. For example, the implantable device can be balloon expanded to facilitate expansion of the frame of the device. This expansion force can ensure that a coated or composite device is able to expand sufficiently, as desired.

In use, an access catheter is advanced within the neurovasculature as is conventional in the art. A suitable microcatheter adaptable for navigation through the tortuous neurovascular space to access the treatment site is disclosed in commonly assigned U.S. Pat. No. 7,507,229, the entire contents of which are hereby incorporated herein.

In some embodiments, the implantable device can be repositioned within the aneurysm as the device is expanding. The repositioning of the device can allow a clinician to position a lower porosity section of the device adjacent to or away from the neck of the aneurysm. The repositioning of the device can also allow a clinician to position a higher average porosity section of the device adjacent to one or more perforating vessels (e.g., perforating arteries or arterials) adjacent to the aneurysm. The repositioning of the device can also allow a clinician to position a lower porosity portion of the device adjacent to a bifurcation. The repositioning of the device can also allow a clinician to position a higher average porosity portion of the device toward or in the fundus of the aneurysm.

Figure 10:
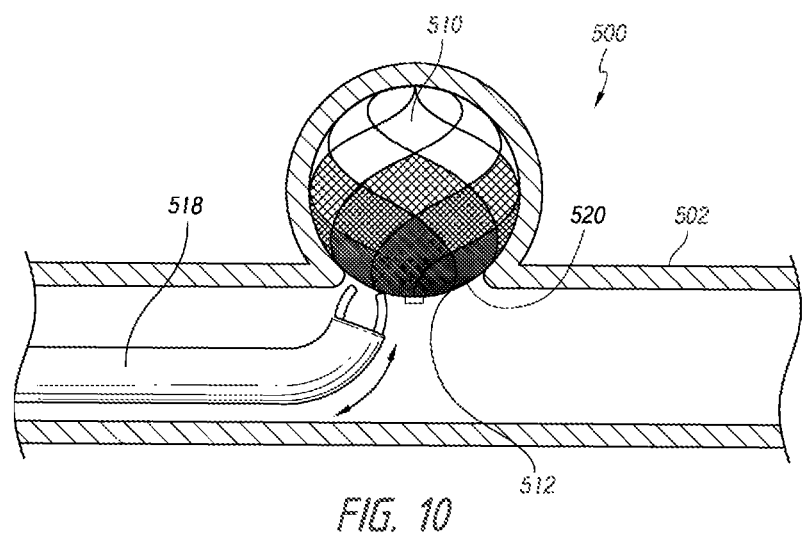
FIGS. 10 and 11 illustrate schematic views of implantable devices that are positioned within aneurysms located along a blood vessel, according to some embodiments.
Figure 11:
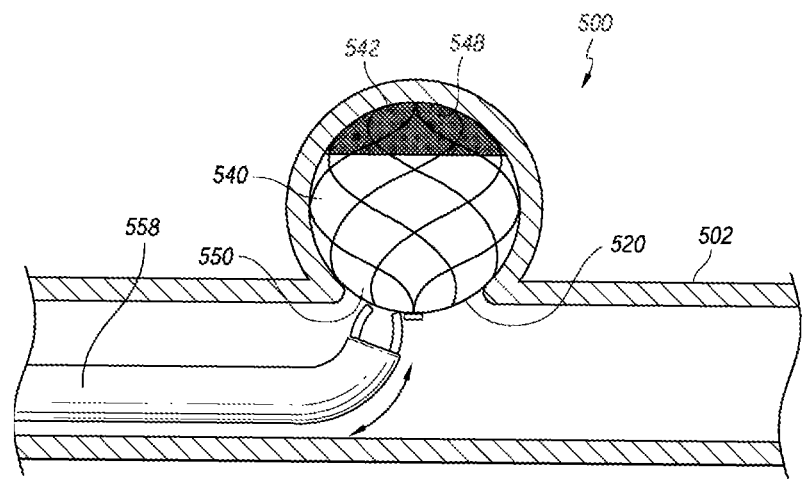

For example, referring now to FIGS. 10 and 11, methods of implanting a medical device can also be performed, in accordance with some embodiments disclosed herein. FIGS. 10 and 11 both illustrate an aneurysm 500 located on a parent vessel 502. FIG. 10 illustrates that a mesh component 512 of the implantable device 510 can be positioned within the aneurysm 500, using a delivery device 518, such that mesh component 512 extends across the ostium 520 of the aneurysm 500. The presence of the mesh component, and the decreased porosity and increased surface area provided thereby, can advantageously decrease blood flow into or out of the aneurysm 500 and encourage endothelialization at the ostium 520.

Similarly, FIG. 11 illustrates an implantable device 540 in which a mesh component 542 of the device is positioned within the aneurysm 500, and more specifically, against a dome 548 of the aneurysm 500 or spaced opposite to or away from the ostium 520. Further, an opposing region of the device, such as a region 550, which can be configured to define a porosity that is relatively less than the porosity of the device along the region occupied by the mesh component 542, can be positioned along the ostium 520 using a delivery device 558. In such an embodiment, placement of the implantable device 540 in this manner can allow endothelialization between the implantable device 540 along the dome 548 of the aneurysm and permit some blood flow into or out of the aneurysm.

Further, in accordance with some embodiments, the implantable device or a portion of the implantable device can be used in conjunction with other treatment modalities. For example, the implantable device can be delivered and subsequently packed with a liquid embolic The injection of a liquid embolic can increase the overall packing density within the implantable device. Additionally, coils can be introduced through an open end or pore of the implantable device.

In implementing a method for placing an implantable device within an aneurysm and injecting coils, expandable components, or other materials into the implantable device, the open end or widest interstices of the implantable device can be positioned at the neck of the aneurysm so as to facilitate insertion of the distal end of the catheter into the open end or between the filaments (i.e., into an interstice) of the implantable device. In embodiments having a braided material for the implantable device, the braid pattern can be properly aligned to facilitate entry of the materials into the implantable device. As in other embodiments disclosed herein, the implantable device can comprise a radiopaque material or component that facilitates visualization and enables the clinician to align the implantable device as needed within the aneurysm.

The composite effect of the coils, expandable components, and/or other materials inserted into the implantable device can provide the advantages and benefits discussed above with respect to various other implantable devices. As such, the clinician can determine and control various intrasaccular implant characteristics, including porosity, composition, material, shape, size, interconnectedness, inter-engagement, coating, etc.

According to some embodiments, systems or kits having an implantable device and at least one coil, expandable component, and/or other material can be provided.

Composite Porosity

In some embodiments, a composite structure of the implantable device can comprise two or three materials having different porosities. Further, the composite structure of the implantable device can comprise for, five, six, or more different materials having different porosities. Some embodiments of the implantable device can be configured to provide a specific porosity profile. The porosity profile can comprise a single, consistent average porosity across the surface of the entire implantable device, or multiple average porosity zones, portions, or regions having different average porosities that collectively form a composite implantable device.

For example, some embodiments can be configured to have a low average surface porosity. For purposes of illustration, high surface porosity is illustrated in the Figures using hexagonal patterns with larger-sized hexagons compared to hexagonal patterns with smaller-sized hexagons, which are used to illustrate medium and low porosity structures. Low surface porosity can provide higher resistance to blood flow therethrough, which can facilitate thrombogenesis. When such low porosity implantable devices are implanted into an aneurysm, such devices can tend to isolate the aneurysm from the parent vessel and minimize blood flow velocity within the aneurysm while supporting the aneurysm wall.

Conversely, as surface porosity increases, blood flow through the implantable device can increase, thereby tending to provide less support for thrombogenesis due to lower resistance to flow therethrough. Nevertheless, the realization of some embodiments disclosed herein is that high porosity structures can also support the aneurysm wall, beneficially aid in healing and thrombogenesis for select aneurysm morphologies, permit flow to other vessels (e.g., branch vessels, perforating arteries, or arterioles), and/or permit the introduction of other materials, such as a liquid embolic, etc.

The porosity of the implantable device may vary along any portion(s) thereof, including any combination of pore sizes of 1 micron or greater. Further, the pores or openings of the frame and mesh component(s) can range from about 1 μm to about 400 μm, from about 5 μm to about 300 μm, from about 8 μm to about 200 μm, from about 10 μm to about 150 μm, from about 15 μm to about 80 μm, or in some embodiments, from about 20 μm to about 50 μm. Further, at least a portion or section of the device can comprise an average porosity of between about 1 μm and about 150 μm. Further, at least a portion or section can comprise an average pore size of between about 100 μm and about 200 μm. Furthermore, at least a portion or section can comprise an average pore size of between about 200 μm and about 300 μm. When an implantable device is formed using multiple sections or portions, each section or portion can have an average porosity within any of the ranges discussed above. Furthermore, a pore size can be calculated using an "inscribed circle" calculation in which size of a given pore is represented by the diameter of the largest circle that fits into the given pore.

Further Embodiments

In accordance with some embodiments, at least a portion of the implantable device can comprise a coating or material for enhancing therapeutic, expansive, or imaging properties or characteristics of at least one or every implantable device.

In some embodiments, the implantable device can be coated with a biocompatible material to promote endothelialization or provide a therapeutic effect.

The coating may include thrombogenic coatings such as fibrin, fibrinogen or the like, anti-thrombogenic coatings such as heparin (and derivatives thereof), urukinase or t-PA, and endothelialization promoting coatings or facilitators such as, e.g., VEGF and RGD peptide, and/or combinations thereof. Drug eluting coatings and a drug eluting foam composite, such as anti-inflammatory or antibiotic, coatings are also envisioned. These drug eluting components may include nutrients, antibiotics, anti-inflammatory agents, anti-platelet agents, anesthetic agents such as lidocaine, and anti-proliferative agents, e.g., taxol derivatives such as paclitaxel. Hydrophilic, hygroscopic, and hydrophobic materials/agents are also envisioned.

Optionally, the implantable device can also comprise an expansion-limiting coating that slows expansion of the device from its natural rate of expansion to a slower rate of expansion such that in the process of expanding, the position of the device can be adjusted within the aneurysm or the device can be removed from the aneurysm, if necessary. Examples of polymers that can be used as expansion-limiting coatings can include hydrophobic polymers, organic non-polar polymers, PTFE, polyethylene, polyphenylene sulfide, oils, and other similar materials.

In embodiments, only specific segments of the implantable device may be embedded or coated with an agent to provide desired characteristics to the implantable device(s). For example, an implantable device can comprise a non-thrombogenic coating may be applied to a lower half of the implantable device to minimize clotting at this location. Such coatings may be desirable in aneurysms located at a bifurcation such that blood flow to branch arteries is permitted through the segment of the foam structure having the non-thrombogenic coating. The coated area may be a different color than the remaining portion of the implantable device to assist the surgeon in identifying this area.

Optionally, the coated area can also comprise radiopaque material to assist the surgeon in visualization and placement of the implantable device in a desired orientation relative to the aneurysm. The implantable device can have radiopacity characteristics either by adding radiopaque filler to the material (which in some embodiments comprises a foam material), such as bismuth, or attaching radiopaque markers. Alternatively, a radiopaque material can be coupled to the implantable device, such as by dipping, spraying, or otherwise mechanically, chemically, or thermally coupled, injected into, or blended into to the implantable device.

Further Aspects of Some Embodiments

The apparatus and methods discussed herein are not limited to the deployment and use of a medical device or stent within the vascular system but may include any number of further treatment applications. Other treatment sites may include areas or regions of the body including any hollow anatomical structures.

The foregoing description is provided to enable a person skilled in the art to practice the various configurations described herein. While the subject technology has been particularly described with reference to the various Figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of manufacturing an implant assembly, comprising:
   closing an end of a tubular braid to form a substantially closed configuration, the tubular braid comprising first filaments that intersect to define first openings, the first filaments and first openings collectively defining a first porosity;

inserting a form into an open end of the tubular braid such that the tubular braid is positioned around the form;

setting a device frame shape based on the form to provide an implant; and coupling a mesh component onto at least a proximal region of the implant, the mesh component comprising second filaments and second openings that collectively define a second porosity permitting blood flow therethrough, the second porosity being less than the first porosity such that blood flow into the implant is more restricted along the proximal region of the implant than along a distal region of the implant.

2. The method of claim 1, wherein each of the first openings has a diameter of from about 1 μm to about 400 μm.

3. The method of claim 1, wherein the frame is expandable from a compressed configuration to an expanded configuration.

4. The method of claim 1, wherein coupling the mesh component onto at least the proximal region of the implant comprises laminating the mesh component onto the tubular braid.

5. The method of claim 1, wherein coupling the mesh component onto at least the proximal region of the implant comprises welding the mesh component to the tubular braid.

6. The method of claim 1, wherein the mesh component is a first mesh component, and wherein coupling further comprises coupling a second mesh component to at least the proximal region of the implant, the second mesh component being separate from the first mesh component and comprising third filaments and third openings that collectively define a third porosity different than the second porosity.

7. The method of claim 6, wherein the second mesh component is coupled to the implant such that the second mesh component abuts or adjoins the first mesh component along the proximal region of the implant.

8. The method of claim 6, further comprising coupling a third mesh component to the implant.

9. The method of claim 1, wherein the implant is configured to be implanted within an aneurysm of a human patient such that the proximal region of the frame coupled to the first mesh component is positioned across an ostium of the aneurysm.

10. The method of claim 1, wherein closing the end of the tubular braid comprises:

collapsing a section of the tubular braid to the substantially closed configuration using a tie, and inverting a first tubular section of the tubular braid over the tie at the section to produce dual layers in the tubular braid such that the tubular braid has a tubular configuration with the closed end at the section and the open end opposite the section.

11. The method of claim 10, further comprising removing the tie from the braid.

12. The method of claim 11, wherein removing the tie comprises burning away the tie during heatsetting.

13. The method of claim 1, further comprising removing the form from the braid.

14. The method of claim 13, wherein removing the form comprises removing the form in one piece.

15. A method of manufacturing an implant assembly, comprising:

providing a braid comprising first filaments and first openings that collectively define a first porosity;

inserting a form into an end of the braid such that the braid is positioned around the form;

coupling a first mesh component onto at least a proximal region of the braid, the first mesh component comprising second filaments and second openings that collectively define a second porosity permitting blood flow therethrough, the second porosity being less than the first porosity, and coupling a second mesh component to at least the proximal region of the braid, the second mesh component comprising third filaments and third openings that collectively define a third porosity different than the second porosity.

16. The method of claim 15, wherein the third porosity is less than the second porosity.

17. The method of claim 15, wherein the second mesh component is coupled to the braid such that the second mesh component abuts or adjoins the first mesh component along the proximal region of the braid.

18. The method of claim 15, wherein the end is a second end, the method further comprising, prior to inserting the form, closing a first end of the braid to form a substantially-closed configuration.

19. The method of claim 18, wherein closing the first end of the braid comprises:

collapsing a section of the braid to the substantially closed configuration using a tie, and inverting a first tubular section of the braid over the tie at the section to produce dual layers in the braid such that the braid has a tubular configuration with the first end at the section and the second end opposite the section.

* * * * *